(12) United States Patent
Di Pietro

(10) Patent No.: US 6,200,291 B1
(45) Date of Patent: Mar. 13, 2001

(54) DEVICE FOR CONTROLLING THE PENETRATION DEPTH OF A NEEDLE, FOR APPLICATION TO AN INJECTION SYRINGE

(76) Inventor: Antonio Di Pietro, Via Plinio 1, 20129, Milano (IT)

( * ) Notice: Subject to any disclaimer, the term of this patent is extended or adjusted under 35 U.S.C. 154(b) by 0 days.

(21) Appl. No.: 09/582,468
(22) PCT Filed: Oct. 2, 1998
(86) PCT No.: PCT/IT98/00262
  § 371 Date: Jun. 26, 2000
  § 102(e) Date: Jun. 26, 2000
(87) PCT Pub. No.: WO99/34850
  PCT Pub. Date: Jul. 15, 1999
(51) Int. Cl.[7] .................................................. A61M 5/00
(52) U.S. Cl. .......................................... 604/117; 604/187
(58) Field of Search .................................. 604/117, 187, 604/263

(56) References Cited

U.S. PATENT DOCUMENTS

| | | | | |
|---|---|---|---|---|
| 1,934,046 | * | 11/1933 | Demarch | 604/187 |
| 4,769,003 | * | 9/1988 | Stamler | 604/187 X |
| 4,898,588 | * | 2/1990 | Roberts | 604/187 |
| 4,978,344 | * | 12/1990 | Dombrowski et al. | 604/263 X |

* cited by examiner

*Primary Examiner*—John D. Yasko
(74) *Attorney, Agent, or Firm*—Hedman & Costigan, P.C.

(57) ABSTRACT

The disclosure relates to a device for controlling or adjusting the penetration depth of a needle, specifically designed for application to an injection syringe, comprising an element designed for contacting a person's skin, said contact element including a surface which encompasses, at least partially, the tip of the needle. The contact element is operatively associated with syringe coupling means and comprises a plurality of throughgoing micro-holes passing through the surface.

3 Claims, 2 Drawing Sheets

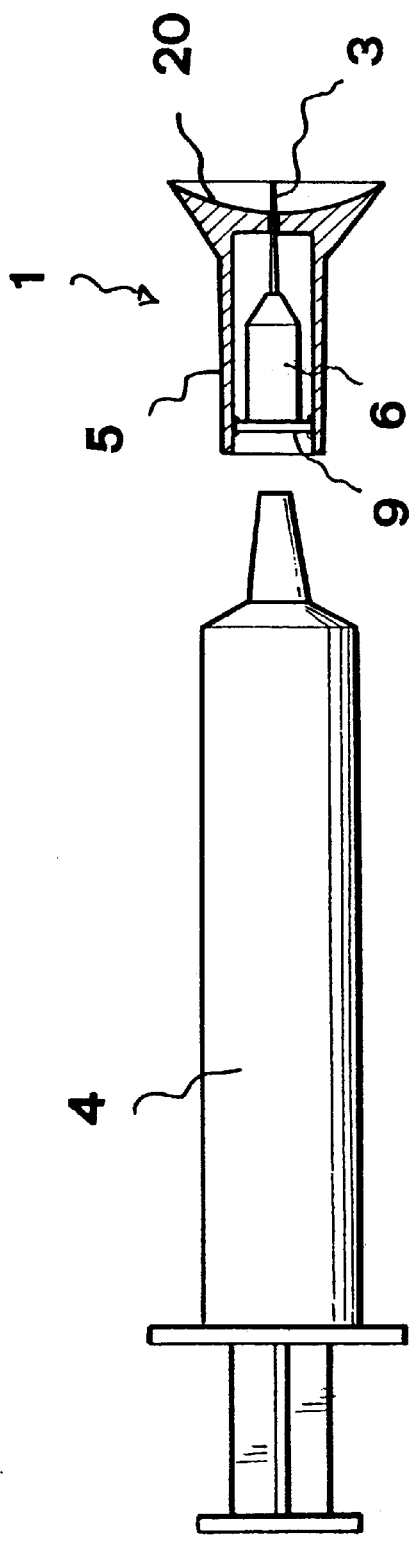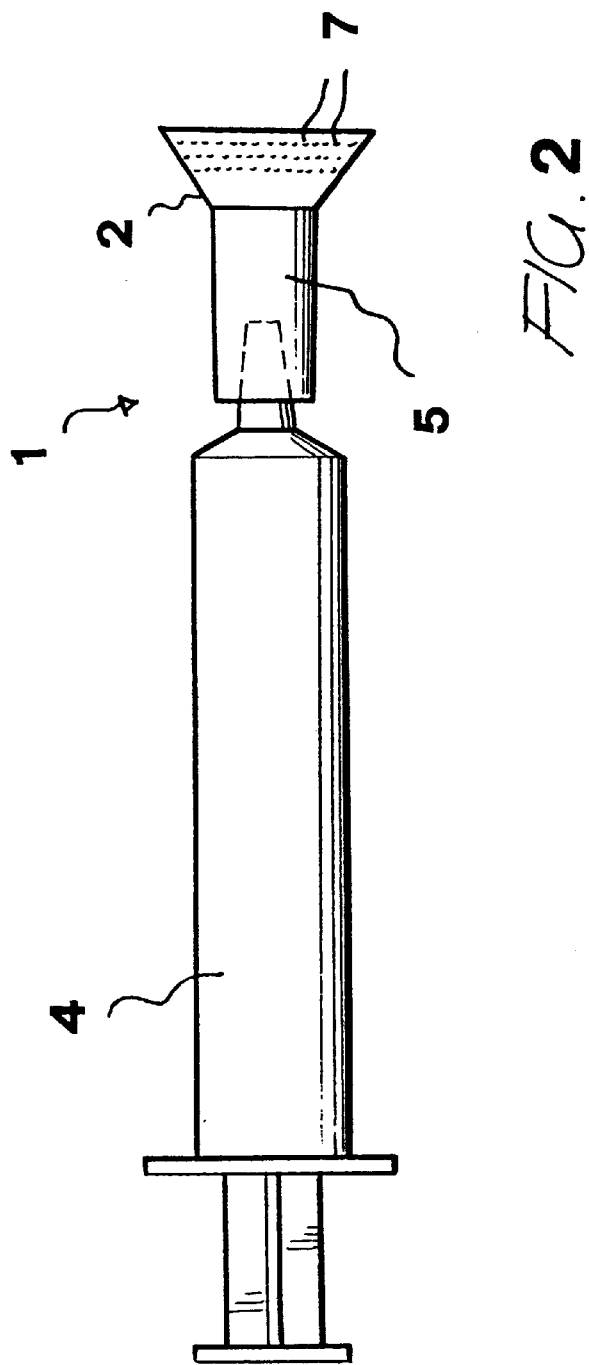

DEVICE FOR CONTROLLING THE PENETRATION DEPTH OF A NEEDLE, FOR APPLICATION TO AN INJECTION SYRINGE

BACKGROUND OF THE INVENTION

The present invention relates to a device for controlling the penetration depth of a needle, for application to an injection syringe.

As is known, several substances are conventionally injected into the human body, for example intracutaneously, i.e. by injections which affect substantially only the surface layer of the human derma.

In particular, for performing the above mentioned injections, it is necessary to cause a syringe needle to enter for a limited length the patient derma.

On the other hand, as prior syringes are used for the above mentioned application, it is difficult to obtain a proper penetration depth of the needle, since this penetration depth substantially depends on the manual skillness of the operator.

In this connection, it should be apparent that an excessive penetration of the syringe needle would originate a disagreable pain feel for the patient, while preventing the injected substance from being properly absorbed.

A further aspect to be considered is that intradermal injection treatments, such as, in particular, those of a dermatological type, would require a comparatively high number of intradermal or intracutaneous injections, thereby the above mentioned problems will recursively occur.

SUMMARY OF THE INVENTION

Accordingly, the aim of the present invention is to provide a device for controlling or adjusting the penetration depth of-a syringe needle, which is specifically designed for application to an intradermal injection syringe, which allows the injections to be performed in an optimum manner.

The above aim is achieved by the present invention providing a device for controlling the penetration depth of a needle, for application to an injection syringe, characterized in that said device comprises a skin contacting element, said skin contacting element including a surface encompassing, at least partially, the tip of said needle, and in that said skin contacting element is operatively associated with coupling means for connection with said syringe.

According to a preferred embodiment of the present invention, the skin contacting element comprises an end tapering portion ending with the above mentioned surface.

Preferably, said surface has a spherical cap configuration and has its concavity facing the needle tip.

Moreover, the needle tip projects for a short length from said surface.

According to a further preferred embodiment of the present invention, the mentioned end tapering portion is provided with a plurality of throughgoing holes passing through said surface.

According to a further preferred embodiment of the invention, the means for coupling the skin contacting element and syringe comprise an outer cylindric body ending with said tapering portion and an inner cylindric body, substantially coaxial to the outer cylindric body supporting the syringe needle.

Finally, the inner cylindric body comprises a circular rim or edge, opposite to the end portion the needle tip projects from, and the circular rim or edge is arranged inside the outer cylindric body.

The invention provides the following advantages, with respect to the prior art.

Firstly, the device according to the present invention allows to accurately adjust the needle penetration depth, without the need of performing manual controlling operations by the operator.

Secondly, the provision of throughgoing microholes or any other throughgoing holes, through the end tapering portion of the device, allows to prevent any suction effect due to the pressure difference between the inside of the tapering portion and the outer atmospheric pressure, thereby allowing air to outflow.

Thus, the syringe will be prevented from adhering to the skin of the patient by its end tapering portion, which would compel the operator to forcibly detach the syringe from the patient.

This suction cup effect would be particularly dangerous in all those cases in which the medical treatment provides a plurality of subsequent injections.

Moreover, the use of a suitably contoured surface, to be slightly pressed against the skin of the patient, will allow to sensitize the region encompassing the needle puncture region, thereby the slight pain feeling affecting the patient during the intradermal injection will be further diluted or reduced, to assure, mainly in a case of a plurality of subsequent injections, a greater pain release for the patient.

Finally, the device according to the present invention can be easily constructed by using easily commercially available elements and materials and, moreover, said device can be used with existing syringes.

BRIEF DESCRIPTION OF THE DRAWINGS

Further advantages and characteristics of the present invention will become more apparent hereinafter from the following disclosure, given by way of an illustrative but not limitative example, with reference to the accompanying drawings, where:

FIG. 1 is a partially cross-sectioned side view of the device for controlling the penetration depth of a needle according to the present invention, and of a syringe the device is associated with;

FIG. 2 is a side view of the syringe assembly fitted to the device for controlling the needle penetration depth;

DESCRIPTION OF THE PREFERRED EMBODIMENTS

Figure 3:
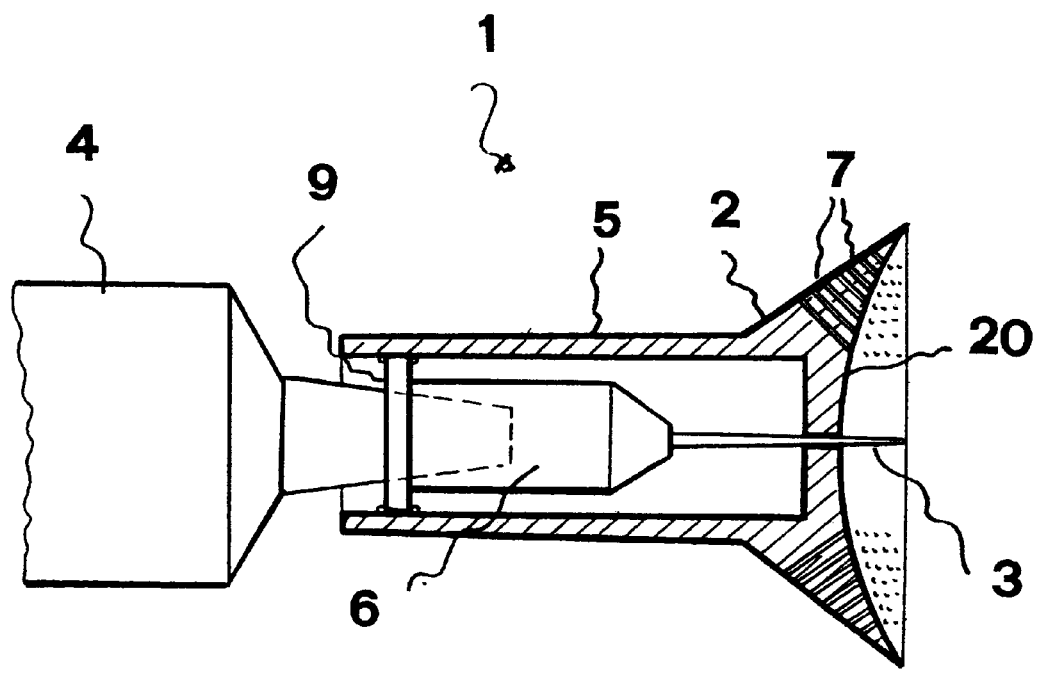
FIG. 3 is a partially cross-sectioned view, on an enlarged scale, of the subject device for controlling the penetration depth of a needle.
Figure 4:
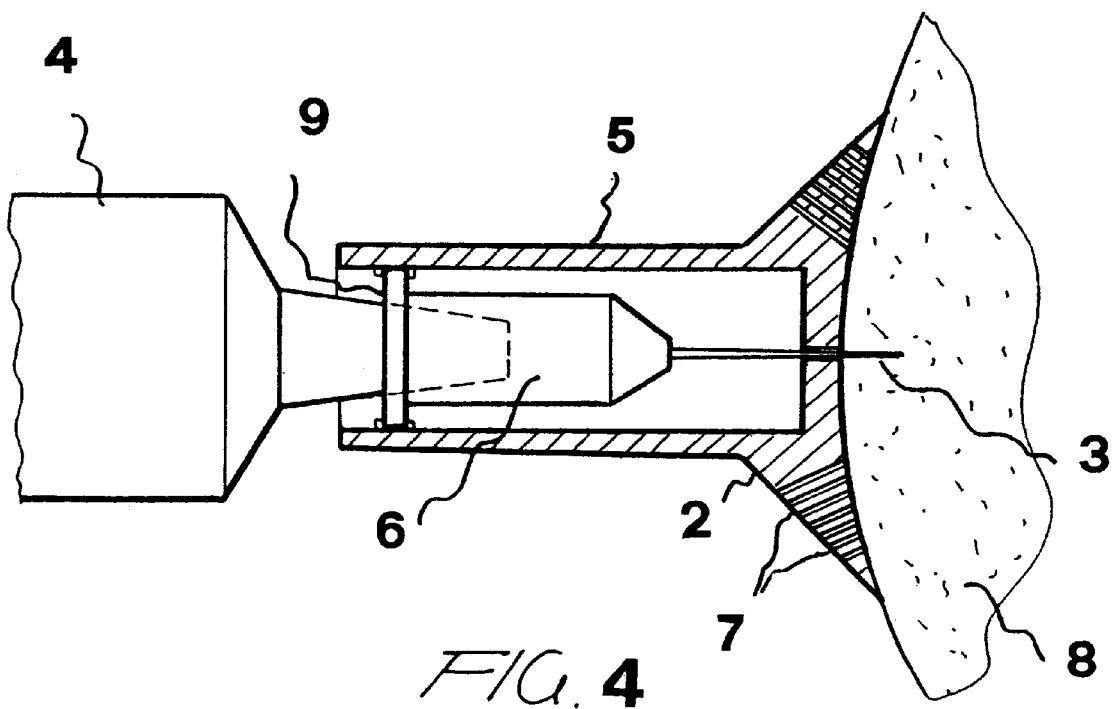
FIG. 4 is a further partially cross-sectioned view, on an enlarged scale, of the subject device for controlling a needle penetration depth, during the carrying out of an intradermal or intracutaneous injection.

In the following disclosure reference will be made to a preferred embodiment of the invention, which will be illustrated as a not limitative example of several possible variations of the invention.

FIG. 1 is a partially cross-sectioned view illustrating the device for controlling the penetration depth of a needle according to the present invention, said device being generally indicated by the reference number 1, this figure further showing a syringe 4 to which said device 1 is coupled.

The device 1, specifically designed for application to said intradermal injection syringe 4, comprises a skin contacting element specifically designed for contacting the skin 8 of a patient, said skin contacting element holding therein a needle 3.

Said skin contacting element 8 comprises a cylindric portion, defining an outer cylindric body 5, and ending with a tapering or conic portion 2.

The tapering portion 2 encompasses the tip of the needle 3 and has, at said needle 3 tip, a surface 20.

Preferably, said surface 20 has a substantially spheric cap configuration, and its concavity is facing the tip of the needle 3.

Moreover, said needle 3 tip projects, for a short length, from the surface 20.

Inside the outer cylindric body 5 an inner cylindric body 6 is provided, which is substantially coaxial to said outer cylindric body 5.

The inner cylindric body 6 supports the needle 3 and is provided with a circular rim or edge 9, opposite to the end therefrom projects the tip of the needle 3, and which is arranged inside the outer cylindric body 5.

Moreover, said tapering portion 2 is provided with a plurality of throughgoing microholes 7 passing through the surface 20.

The device 1 for controlling the penetration depth of a needle according to the present invention operates a follows.

More specifically, the device 1 is applied to contact the skin 8 of the patient, i.e. such that the edge of the surface 20 would be brought into contact with the patient skin 8.

In this position, the device 1 is slightly pressed to cause the skin 8 to be slightly deformed in order to allow the needle 3 to enter the skin for a set length.

Then, the substance held in the syringe 4 will be injected into the patient skin 8, according to a per se known manner, by pressing on the syringe 4 plunger.

Upon ending the intradermal injection, the device 1 will be moved away from the patient skin 8 thereby allowing the skin to resiliently recover to its starting configuration, to favor the injected substance to be easily absorbed by the derma and, then, in the blood system.

In this connection it should be pointed out that the provision of the above mentioned microholes 7, or any other throughgoing holes, through the tapering portion 2 of the device 1 will prevent any suction cup effect due to a pressure difference between the inside of the tapering portion 2 and the outer atmospheric pressure from occurring.

In fact, said microholes 7, or any other types of throughgoing holes to be formed through the tapering portion 2, will allow air to outflow as the intradermal injection is carried out.

Thus, the syringe 4 will be prevented from adhering to the patient skin with its end tapering portion 2, which adhesion would compel the operator to forcibly detach the syringe from the skin of the patient.

The mentioned suction cup effect would be particularly dangerous in those cases in which the treatment would provide a plurality of subsequent injections.

Moreover, since the edge or rim of the surface 20 is slightly pressed against the skin 8 of the patient, this would allow the area encompassing the needle 3 puncture to be sensitized thereby the slight pain feeling affecting the patient during the intradermal injection will be further reduced, while assuring a greater pain release to the patient, mainly in the case of repeated injections.

What is claimed is:

1. A device (1) for controlling the penetration depth of a needle (3), for application to an injection syringe (4), said device (4) comprising a skin contacting element (8), encompassing, at least partially, the tip of said needle (3), said skin contacting element (8) being operatively associated with coupling means for connection with said syringe (4), characterized in that said skin contacting element (8) comprises an end tapering conic portion (2) ending with a surface (20), having a spheric cap configuration and presenting the concavity thereof facing the needle tip projecting for a short length from said surface (20), and that said tapering conic portion (2) comprises a plurality of throughgoing microholes (7) passing through said surface (20).

2. A device according to claim 1, characterized in that said means for coupling said skin contacting element (8) to said syringe (4) comprise an outer cylindric body (5) ending with said tapering portion (20) and an inner cylindric body (6), substantially coaxial to said outer cylindric body (5) and supporting said needle (3).

3. A device according to claim 2, characterized in that said inner cylindric body (6) is provided with a circular rim (9), opposite to the end portion therefrom said tip of said needle (3) projects, wherein said circular rim (9) is arranged inside said outer cylindric body (5).

\* \* \* \* \*